United States Patent [19]

Ohashi et al.

[11] Patent Number: 5,023,364

[45] Date of Patent: Jun. 11, 1991

[54] PHENOXYALKYLCARBOXYLIC ACID DERIVATIVES AND PROCESS FOR THEIR PREPARATION

[75] Inventors: Mitsuo Ohashi, Ohmiya; Katsuya Awano, Oyama; Toshio Tanaka; Tetsuya Kimura, both of Tochigi, all of Japan

[73] Assignee: Kyorin Pharmaceutical Co., Ltd., Tokyo, Japan

[21] Appl. No.: 325,007

[22] Filed: Mar. 17, 1989

Related U.S. Application Data

[63] Continuation-in-part of Ser. No. 241,262, Sep. 7, 1988, abandoned.

[30] Foreign Application Priority Data

Sep. 10, 1987 [JP] Japan .................................. 62-226940

[51] Int. Cl.$^5$ .............................................. C07C 69/76
[52] U.S. Cl. ..................................... 560/53; 562/464; 514/543; 514/571
[58] Field of Search .......................... 560/53; 562/464; 514/543, 571

[56] References Cited

U.S. PATENT DOCUMENTS 4,782,176 11/1988 Carson ............................... 562/464

FOREIGN PATENT DOCUMENTS 2118184 10/1983 United Kingdom .................. 560/53

Primary Examiner—Paul J. Killos
Attorney, Agent, or Firm—Oblon, Spivak, McClelland, Maier & Neustadt

[57] ABSTRACT

Phenoxyalkylcarboxylic acid derivatives of the following formula,

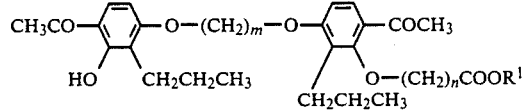

wherein $R^1$ indicates a hydrogen atom, a methyl group or an ethyl group, m is equal to 2, 3 or 4, and n is equal to 3 or 4, their alkali salts and hydrates thereof are useful as antiallergic agents.

6 Claims, No Drawings

PHENOXYALKYLCARBOXYLIC ACID DERIVATIVES AND PROCESS FOR THEIR PREPARATION

This is a continuation-in-part of application Ser. No. 07/241,262 filed on Sept. 7, 1988 now abandoned.

DETAILED DESCRIPTION OF THE INVENTION

This invention is concerned with certain novel phenoxyalkylcarboxylic acid derivatives, which have a strong and selective anti-leukotriene action and are useful for the prevention or treatment of allergic diseases such as asthma, their intermediates and process for their preparation thereof.

Moreover, it relates to certain novel phenoxyalkylcarboxylic acid derivatives of the formula (I).

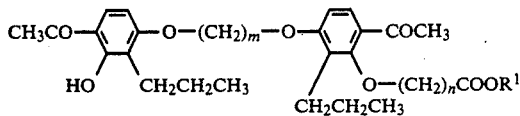

(I)

wherein $R^1$ indicates a hydrogen atom, a methyl group or an ethyl group, m is equal to 2, 3 or 4, and n is equal to 3 or 4, their alkali salts and hydrates thereof.

Leukotrienes (leukotriene $C_4$, $D_4$ and $E_4$), which are metabolites of arachidonic acid through 5-lipoxygenase pathway, are constituents of SRS-A (slow reacting substance of anaphylaxis), being an important mediator of the immediate type allergic disease such as bronchial asthma. For this reason, the drugs which antagonize leukotrienes are promising in the treatment of allergic diseases. However, only few drugs having those effects through the internal use are known and none is practically used.

In the previous patent (Japan Patent Kokai No. 58-189137 corresponding to U.S. Pat. No. 4,507,498), [6-acetyl-3-[3-(4-acetyl3-hydroxy-2-propylphenoxy)-propoxy]-2-propylphenoxy]acetic acid is disclosed in one concrete example of that patent, and all of the other examples disclose 4-acetyl-3-substituted-2-propylphenoxyacetic acids, while the compounds disclosed in the previous patent are not useful as leukotriene antagonists because of their low potency.

As the result of diligent studies about leukotriene antagonists, the inventors have found that the compounds represented by the general formula (I) have a strong and selective inhibitory action on leukotriene $D_4$-induced bronchoconstriction by an oral administration. Surprisingly, these compounds showed the marked inhibition also on airway hypersensitivity in guinea pigs.

The compounds represented by the general formula (I) are, for example, 4-[6-acetyl-3-[2-(4-acetyl-3-hydroxy-2-propylphenoxy)-ethoxy]-2-propylphenoxy]-butanoic acid, 4-[6-acetyl-3-[3-(4-acetyl-3-hydroxy-2-propylphenoxy)propoxy]-2-propylphenoxy]butanoic acid, 4-[6-acetyl-3-[4-(4-acetyl-3-hydroxy-2-propyl-phenoxy)butoxy]-2-propylphenoxy]butanoic acid, 5-[6-acetyl-3-[3(4-acetyl-3-hydroxy-2-propylphenoxy)-propoxy]-2-propylphenoxy]pentanoic acid.

According to the present invention, the compounds represented by the general formula (I) are prepared by the following routes.

(1) The compounds wherein $R_1$ is a hydrogen atom in the general formula (I) can be prepared by hydrolyzing the compounds represented by the general formula (Ia). Typically, they can be prepared by heating the compounds represented by the general formula (Ia) with alkaline solution such as, for example, sodium hydroxide, potassium hydroxide, under stirring.

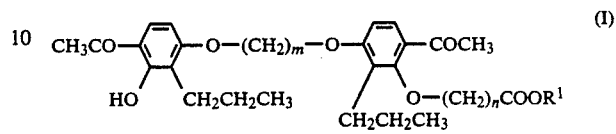

(I)

wherein, m and n are same as described above.

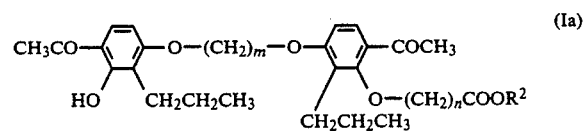

(Ia)

wherein $R^2$ indicates a methyl group or an ethyl group, m and n are same as described above.

(2) The compounds represented by the general formula (Ia) can be prepared by allowing the compounds represented by the general formula (III) to react with the compounds represented by the general formula (II). Typically, they can be prepared by allowing the compounds represented by the general formula (III) to react with the compounds represented by the general formula (II) in organic solvents such as, for example, acetone, methylethylketone, diethylketone, dimethylformamide, in the presence of bases such as, for example, potassium carbonate, sodium carbonate, the reaction temperature is preferably between room temperature and reflux temperature. The addition of catalysts such as for example, potassium iodide is preferable.

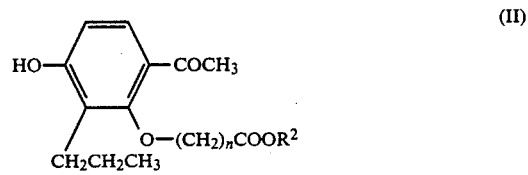

(II)

wherein $R^2$ and n are same as described above.

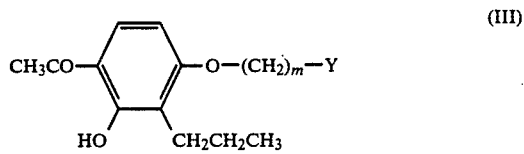

(III)

wherein m is same as described above and Y indicates a leaving group.

Y represented by the general formula (III) is preferably a halogen atom such as, for example, a chlorine or bromine atom.

(3) The compounds represented by the general formula (Ia) can be also prepared by allowing the compounds represented by the formula (V) to react with the compounds represented by the general formula (IV). Typically, they can be prepared by allowing the compounds represented by the formula (V) to react with the compounds represented by the general formula (IV) in organic solvent such as, for example, acetone, methylethylketone, diethylketone, dimethylformamide and so on, in the presence of bases such as, for example, potassium carbonate, sodium carbonate, at a temperature in the range of room temperature to reflux temperature. The addition of catalysts such as, for example, potassium iodide is preferable.

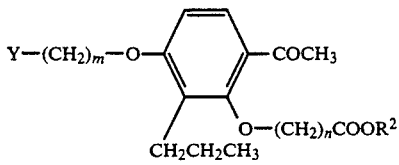

(IV)

wherein $R^2$, m and n are same as described above and Y indicates a leaving group.

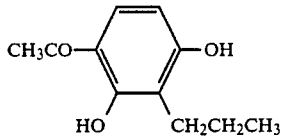

(V)

Y represented by the general formula (IV) is preferably a halogen atom such as, for example, a chlorine or bromine atom.

(4) The compounds represented by the general formula (II) can be prepared by removing a protecting group from the compounds represented by the general formula (VIII). The compounds represented by the general formula (VIII) can be prepared by allowing the compounds represented by the general formula (VII) to react with the compounds represented by the general formula (VI) in organic solvents such as, for example, acetone, methylethylketone, diethylketone, dimethylformamide, at a temperature in the range of room temperature to reflux temperature presence of bases such as, for example, potassium carbonate, sodium carbonate, and addition of potassium iodide to the reaction mixture are preferable.

$R^3$ shown in the general formula (VI) and (VIII) is a protecting group such as, for example, benzyl group, methoxymethyl group. When the protecting group is benzyl group, the compounds represented by the general formula (II) can be prepared by hydrogenolysis using palladium-chacoal.

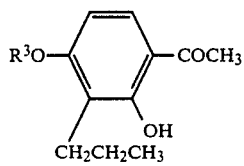

(VI)

wherein $R^3$ indicates a protecting group.

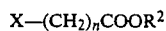

(VII)

wherein $R^2$, n are same as described above and X indicates a leaving group.

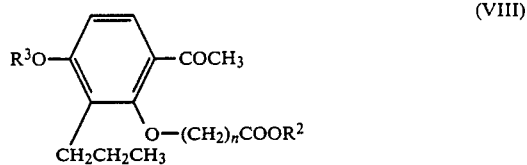

(VIII)

wherein $R^2$, $R^3$ and n are same as described above.

X in the general formula (VII) is preferably halogen atom such as, for example, a chlorine or bromine atom.

In following, the invention will be illustrated based on concrete examples, but the invention is not confined solely to these examples.

EXAMPLE 1

Ethyl 4-[6-acetyl-3-[3-(4-acetyl-3-hydroxy-2-propylphenoxy)propoxy]-2-propylphenoxy]butanoate 1) Ethyl 4-(6-acetyl-3-benzyloxy-2-propylphenoxy)-butanoate A mixture of 4'-benzyloxy-2'-hydroxy-3'-propylacetophenone (3.0 g), anhydrous potassium carbonate (2.9 g), potassium iodide (0.5 g) in N,N-dimethylformamide (40 ml) was stirred at 100° C. To this mixture was added ethyl 4-bromobutyrate (3.1 g) dropwise under stirring and the mixture was stirred for 8 hours. This mixture was poured into ice water and extracted with ethyl acetate. The organic layer was washed with water, dried over anhydrous sodium sulfate and evaporated. The resulting residue was purified by silica gel column chromatography, eluting with benzene-ethyl acetate (20:1), to give the title compound (2.2 g, 52.3%) as brown oil.

$^1$H-NMR (CDCl$_3$) δ: 0.98 (3H, t, J=7 Hz, -CH$_2$CH$_2$C$\underline{H}$$_3$), 1.27 (3H, t, J=7 Hz, COOCH$_2$C$\underline{H}$$_3$), 1.60 (2H, m, CH$_2$C$\underline{H}$$_2$CH$_3$), 2.14 (2H, m, OCH$_2$C$\underline{H}$$_2$CH$_2$COOEt), 2.50 (2H, t, J=6 Hz, C$\underline{H}$$_2$COOEt), 2.58 (3H, s, COC$\underline{H}$$_3$), 2.66 (2H, t, J=7 Hz, C$\underline{H}$$_2$CH$_2$ CH$_3$), 3.81 (2H, t, J=6 Hz, OC$\underline{H}$$_2$CH$_2$CH$_2$COOEt), 4.15 (2H, q, J=7 Hz, COOC$\underline{H}$$_2$CH$_3$), 5.11 (2H, s, PhC$\underline{H}$$_2$), 6.71

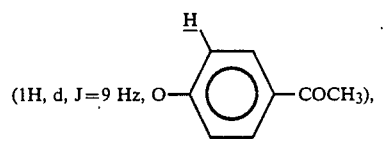

7.38 (5H, m, Ph), 7.51

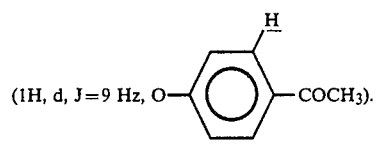

2) Ethyl 4-(6-acetyl-3-hydroxy-2-propylphenoxy)-butanoate

A solution of ethyl 4-(6-acetyl-3-benzyloxy-2-propylphenoxy)butanoate (2.2 g) in ethanol (30 ml) was hydrogenated over 10% palladium on activated carbon (0.45 g) under atmospheric pressure at room temperature. After hydrogen absorption ceased, the catalyst was removed and the solution was evaporated. The residue was purified by silica gel column chromatography, eluting with benzene-ethyl acetate (1:4), to give the title compound (1.2 g, 70.5%) as yellow oil.

$^1$H-NMR (CDCl$_3$) δ: 0.98 (3H, t, J=7 Hz, -CH$_2$CH$_2$C$\underline{H}$$_3$), 1.27 (3H, t, J=7 Hz, COOCH$_2$C$\underline{H}$$_3$), 1.54 (2H, m, CH$_2$C$\underline{H}$$_2$CH$_3$), 2.14 (2H, m, OCH$_2$C$\underline{H}$$_2$CH$_2$COOEt), 2.51 (2H, m, C$\underline{H}$$_2$COOEt), 2.58 (3H, s, COC$\underline{H}$$_3$), 2.60 (2H, m, C$\underline{H}$$_2$CH$_2$CH$_3$), 3.80 (2H, t, J=6 Hz, OC$\underline{H}$$_2$CH$_2$CH$_2$COOEt), 4.16 (2H, q, J=7 Hz, COOC$\underline{H}$$_2$CH$_3$), 6.62

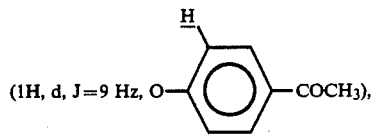

7.43

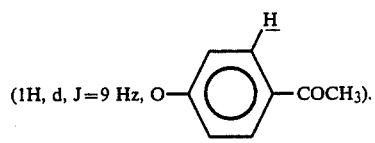

3) Ethyl 4-[6-acetyl-3-[3-(4-acetyl-3-hydroxy-2-propylphenoxy)propoxy]-2-propylphenoxy]butanoate acetophenone (1.35 g) in acetone (10 ml) was added dropwise with stirring to a refluxing mixture of ethyl 4-(6-acetyl-3-hydroxy-2-propyl A solution of 4'-(3-bromopropoxy)-2'-hydroxy-3'-propylphenoxy)butanoate (1.2 g), anhydrous potassium carbonate (0.7 g), potassium iodide (0.5 g) in acetone (50 ml). After 5 hours, additional anhydrous potassium carbonate (0.5 g) was added and the mixture was refluxed for an additional 13 hours. The mixture was filtered off and the solvent was evaporated. The resulting residue was purified by silica gel column chromatography. eluting with benzene-ethyl acetate (4:1), to give the title compound (1.7 g, 80.5%) as colorless crystals, mp 77°-79° C.

Analysis (%) for C$_{31}$H$_{42}$O$_8$, Calcd. (Found): C, 68.61 (68.66); H, 7.80 (7.75).

EXAMPLE 2

Ethyl 5-[6-acetyl-3-[3-(4-acetyl-3-hydroxy-2-propylphenoxy)propoxy]-2-propylphenoxy]pentanoate 1) Ethyl 5-(6-acetyl-3-benzyloxy-2-propylphenoxy)-pentanoate This compound was prepared similarly to example 1-1) and obtained as brown oil (39.2%).

$^1$H-NMR (CDCl$_3$) δ: 0.98 (3H, t, J=7 Hz, -CH$_2$CH$_2$C$\underline{H}$$_3$), 1.26 (3H, t, J=7 Hz, COOCH$_2$C$\underline{H}$$_3$), 1.56 (2H, m, CH$_2$C$\underline{H}$$_2$CH$_3$), 1.85 (4H, m, OCH$_2$C$\underline{H}$$_2$CH$_2$CH$_2$COOEt), 2.40 (2H, m, C$\underline{H}$$_2$COOEt), 2.58 (3H, s, COC$\underline{H}$$_3$), 2.69 (2H, m, C$\underline{H}$$_2$CH$_2$CH$_3$), 3.77 (2H, m, OC$\underline{H}$$_2$(CH$_2$)$_3$COOEt), 4.13 (2H, q, J=7 Hz, COOC$\underline{H}$$_2$CH$_3$), 5.10 (2H, s, PhC$\underline{H}$$_2$), 6.70

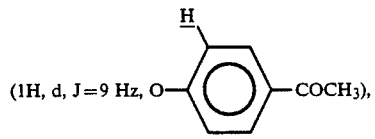

7.37 (5H, m, Ph), 7.50

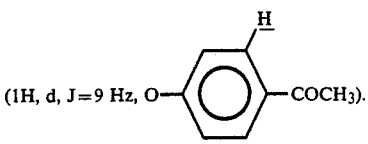

2) Ethyl 5-(6-acetyl-3-hydroxy-2-propylphenoxy)-pentanoate

This compound was prepared similarly to example 1-2) and obtained as brown oil (97.1%).

$^1$H-NMR (CDCl$_3$) δ: 0.98 (3H, t, J=7 Hz, -CH$_2$CH$_2$C$\underline{H}$$_3$), 1.23 (3H, t, J=7 Hz, COOCH$_2$C$\underline{H}$$_3$), 1.54 (2H, m, CH$_2$C$\underline{H}$$_2$CH$_3$), 1.85 (4H, m, OCH$_2$C$\underline{H}$$_2$CH$_2$CH$_2$COOEt), 2.30 (2H, m, C$\underline{H}$$_2$COOEt), 2.59 (3H, s, COC$\underline{H}$$_3$), 2.60 (2H, m, C$\underline{H}$$_2$CH$_2$CH$_3$), 3.77 (2H, m, OC$\underline{H}$$_2$(CH$_2$)$_3$COOEt), 4.15 (2H, q, J=7 Hz, COOC$\underline{H}$$_2$CH$_3$), 6.63

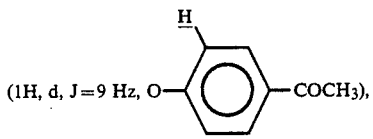

7.42

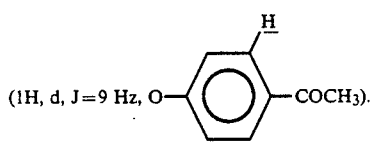

3) Ethyl 5-[6-acetyl-3-[3-(4-acetyl-3-hydroxy-2-propylphenoxy)propoxy]-2-propylphenoxy]pentanoate This compound was prepared similarly to example 1-3) and obtained as yellow oil (57.9%).

$^1$H-NMR (CDCl$_3$) δ: 0.90 (3H, t, J=7 Hz, -CH$_2$CH$_2$C$\underline{H}$$_3$), 0.94 (3H, t, J=7 Hz, -CH$_2$CH$_2$C$\underline{H}$$_3$), 1.26 (3H, t, J=7 Hz, COOCH$_2$C$\underline{H}$$_3$), 1.52 (4H, m, CH$_2$C$\underline{H}$$_2$CH$_3$×2), 1.83 (4H, m, OCH$_2$C$\underline{H}$$_2$CH$_2$CH$_2$COOEt), 2.36 (4H, m, C$\underline{H}$$_2$COOEt, OCH$_2$C$\underline{H}$$_2$CH$_2$O), 2.50 (2H, m, C$\underline{H}$$_2$CH$_2$CH$_3$), 2.56 (3H, s, COC$\underline{H}$$_3$), 2.57 (3H, s, COC$\underline{H}$$_3$), 2.60 (2H, m, C$\underline{H}$$_2$CH$_2$CH$_3$). 3.75 (2H, m, OC$\underline{H}$$_2$(CH$_2$)$_3$COOEt), 4.13 (2H, q, J=7 Hz, COOC$\underline{H}$$_2$CH$_3$), 4.24 (4H, m, OC$\underline{H}$$_2$CH$_2$CH$_2$O), 6.45 and 6.67

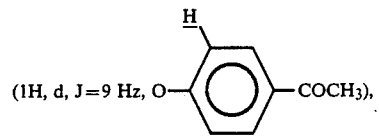

7.51 and 7.58

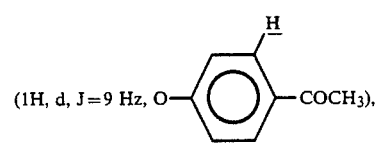

12.72 (1H, s, OH).

EXAMPLE 3

Ethyl 4-[6-acetyl-3-[2-(4-acetyl-3-hydroxy-2-propylphenoxy)ethoxy]-2-propylphenoxy]butanoate The title compound was prepared similarly to example 1-3) and obtained as brown oil (52.5%).

EXAMPLE 4

Ethyl 4-[6-acetyl-3-[4-(4-acetyl-3-hydroxy-2-propylphenoxy)butoxy]-2-propylphenoxy]butanoate The title compound was prepared similarly to example 1-3) and obtained as brown oil (60.9%).

$^1$H-NMR (CDCl$_3$) δ: 0.93 and 0.97 (3H, t, J=7 Hz, -CH$_2$CH$_2$CH$_3$), 1.27 (3H, t, J=7 Hz, COOCH$_2$CH$_3$), 1.56 (4H, m, CH$_2$CH$_2$CH$_3$×2), 2.04 (4H, m, OCH$_2$CH$_2$CH$_2$CH$_2$O), 2.14 (2H, m, OCH$_2$CH$_2$CH$_2$COOEt), 2.51 (4H, m, CH$_2$COOEt, CH$_2$CH$_2$CH$_3$), 2.56 and 2.58 (3H, s, COCH$_3$), 2.65 (2H, m, CH$_2$CH$_2$CH$_3$), 3.80 (2H, t, J=6 Hz, OCH$_2$CH$_2$CH$_2$COOEt), 4.10 (4H, m, OCH$_2$CH$_2$CH$_2$CH$_2$O), 4.16 (2H, q, J=7 Hz, COOCH$_2$CH$_3$), 6.44 and 6.66

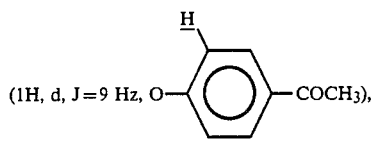

7.53 and 7.58

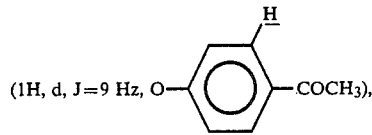

12.74 (1H, s, OH).

EXAMPLE 5

4-[6-Acetyl-3-[3-(4-acetyl-3-hydroxy-2-propylphenoxy)propoxy]-2-propylphenoxy]butanoic acid To a solution of ethyl 4-[6-acetyl-3-[3-(4-acetyl-3-hydroxy-2-propylphenoxy)propoxy]-2-propylphenoxy]butanoate (example 1, 1.7 g) in ethanol (5 ml) was added a solution of sodium hydroxide (0.38 g) in water (5 ml). The mixture was heated on water-bath for 10 minutes, poured into ice water, made acidic with concentrated hydrochloric acid solution and extracted with ethyl acetate. The organic layer was washed with water, dried over anhydrous sodium sulfate and evaporated. The resulting residue was purified by silica gel column chromatography, eluting with dichloromethane-methanol (10:1). Recrystallization from benzene-n-hexane afforded the title compound (0.99 g, 61.4%) as colorless crystals, mp 50°–53° C.

Analysis (%) for C$_{29}$H$_{38}$O$_8$, Calcd. (Found): C, 67.69 (67.76); H, 7.44 (7.40).

EXAMPLE 6–8

Other new compounds (Example 6–8) which were prepared by the same procedure as in Example 5 are listed in Table 1.

TABLE 1

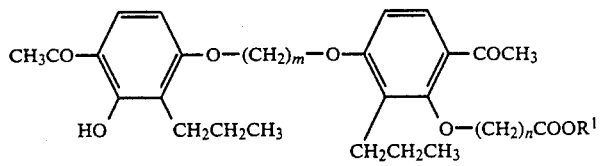

| Example | R$^1$ | m | n | Yield (%) | mp (°C.) | Analysis (%) Calcd./Found |   |   |   |
|---------|-------|---|---|-----------|----------|---|---|---|---|
| 6 | H | 2 | 3 | 69.8 | 86–88 | C: | 67.18 | H: | 7.25 |
|   |   |   |   |      |        |    | 66.90 |    | 7.27 |
| 7 | H | 3 | 4 | 87.9 | 62–64 | C: | 68.16 | H: | 7.63 |
|   |   |   |   |      |        |    | 68.21 |    | 7.65 |
| 8 | H | 4 | 3 | 72.2 | 47–48 | C: | 68.16 | H: | 7.63 |
|   |   |   |   |      |        |    | 68.00 |    | 7.58 |

EXPERIMENT 1

Inhibition of bronchoconstriction in guinea pigs

Male Hartley guinea pig weighing about 450 g was anesthetized with sodium pentobarbital (30 mg/kg,i.p.), and the changes in transpulmonary pressure was measured by modifying the method of Konzett-Rossler (J. Harvey, et al., J. Pharmacol. Method. 9, 147–155, 1983) under an artificial ventilation. Bronchoconstrictor response was induced by bolus injection of leukotriene D$_4$ (3 μg/kg,i.v.) from jugular vein. Animal was treated with indomethacin (10 mg/kg,i.v.) and propranolol (1 mg/kg,i.v.) before leukotriene D$_4$ challenge. Test compounds suspended in 5% Gum Arabic solution were administered orally 2 hours before leukotriene D$_4$ challenge. The results are shown in Table 2.

TABLE 2

| Example | Dose (mg/kg, p.o.) | Inhibition (%) |
|---------|--------------------|-----------------|
| 5 | 1.5 | 27.4 |
|   | 6.25 | 41.7 |
|   | 12.5 | 59.0 |
|   | 50 | 82.7 |
| 6 | 12.5 | 28.6 |
|   | 50 | 86.6 |
| 7 | 12.5 | 45.2 |
|   | 50 | 94.8 |
| 8 | 50 | 83.1 |
| Ref. 1 | 12.5 | −12.1 |
|   | 50 | 56.1 |
| Ref. 2 | 50 | 16.9 |

Ref. 1: [6-Acetyl-3-[3-(4-acetyl-3-hydroxy-2-propylphenoxy)-propoxy]-2-propylphenoxy]acetic acid
Ref. 2: [4-Acetyl-3-[5-(4-acetyl-3-hydroxy-2-propylphenoxy)-pentyloxy]-2-propylphenoxy]acetic acid (described in Japan Tokkyo Kokai 58-189137 corresponding to U.S. Pat. No. 4,507,498).

The compounds of the invention not only antagonized leukotriene D$_4$ in isolated guinea pig ileum and trachea but also inhibited leukotriene D$_4$-induced bronchoconstriction at oral doses lower than that of the reference compound.

Accordingly, the compounds of the invention are useful for the diseases in which leukotrienes play an important role, such as bronchial asthma, allergy in eye, nose and gastrointestinal tract, urticaria, cardiovascular disorders, and so on.

What is claimed is:

1. Phenoxyalkylcarboxylic acid derivatives represented by the following general formula (I),

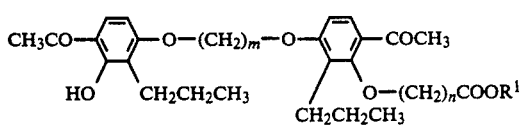

wherein R[1] indicates a hydrogen atom, a methyl group or an ethyl group, m is equal to 2, 3 or 4, and n is equal to 3 or 4; their alkali salts and hydrates thereof.

2. A process for the preparation of the compounds represented by the following general formula (Ia),

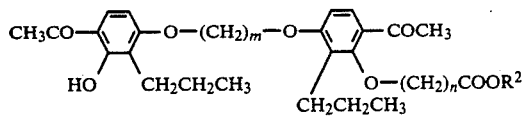

wherein R[2] indicates a methyl group or an ethyl group, and m and n have the same meanings specified in claim 1; their alkali salts and hydrates thereof, which comprises reacting the compounds represented by the following general formula (II),

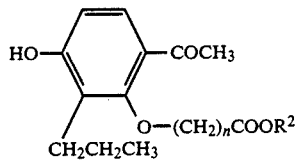

wherein R[2] has the meanings specified above and n has the meanings specified in claim 1, with the compounds represented by the following general formula (III),

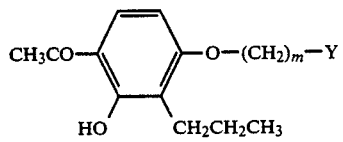

wherein m has the meanings specified in claim 1 and Y indicates a leaving group.

3. A process for the preparation of the compounds represented by the following general formula (Ia),

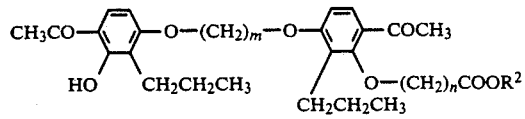

wherein R[2], m and n have the meanings specified in claim 1 and 2; their alkali salts and hydrates thereof, which comprises reacting the compounds represented by the following general formula (IV),

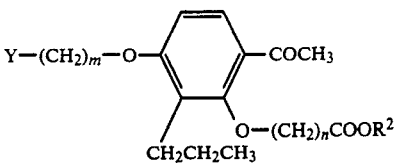

wherein R[2], m and n have the meaning specified in claim 1 and 2, and Y indicates a leaving group with the compounds represented by the following formula (V),

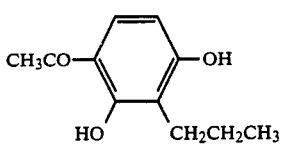

4. A process for the preparation of the compounds represented by the following general formula (II),

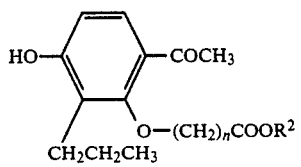

wherein R[2] and n have the meanings specified in claim 1 and 2; their alkali salts and hydrates thereof, which comprises removing the protecting group from the compounds which can be prepared by reacting the compounds represented by the following general formula (VI),

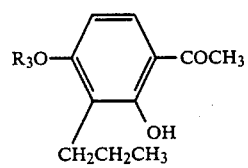

wherein R[3] indicates a protecting group, with the compounds represented by the following general formula (VII),

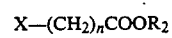

X—(CH$_2$)$_n$COOR$_2$ (VII)

wherein R[2] and n have the meanings specified in claim 1 and 2, and X indicates a leaving group.

5. A process for the preparation of the compounds represented by the following general formula (I), wherein R[1] indicates a hydrogen atom in claim 1, their alkali salts and hydrates thereof, which comprises hydrolyzing the compounds represented by the following general formula (Ia),

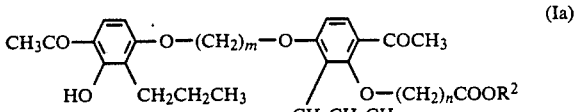

wherein R[2], m and n have the meanings specified in claim 1 and 2.

6. Antiallergics which comprise at least one compound as active component in phenoxyalkylcarboxylic acid derivatives or their alkali salts and hydrates thereof represented by the following general formula (I),
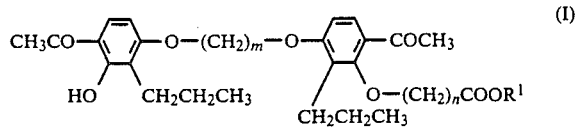
wherein $R^1$, m and n have the meanings specified in claim 1.
* * * * *